(12) United States Patent
Linderman et al.

(10) Patent No.: US 10,314,574 B2
(45) Date of Patent: Jun. 11, 2019

(54) ADHESIVE-COATED SUTURES

(71) Applicant: Washington University, St. Louis, MO (US)

(72) Inventors: Stephen W. Linderman, St. Louis, MO (US); Guy M. Genin, St. Louis, MO (US); Stavros Thomopoulos, St. Louis, MO (US)

(73) Assignee: Washington University, St. Louis, MO (US)

( * ) Notice: Subject to any disclaimer, the term of this patent is extended or adjusted under 35 U.S.C. 154(b) by 257 days.

(21) Appl. No.: 14/940,541

(22) Filed: Nov. 13, 2015

(65) Prior Publication Data

US 2016/0135809 A1    May 19, 2016

Related U.S. Application Data

(60) Provisional application No. 62/079,965, filed on Nov. 14, 2014.

(51) Int. Cl.
| | | |
|---|---|---|
| *A61B 17/00* | (2006.01) | |
| *A61B 17/04* | (2006.01) | |
| *A61B 17/06* | (2006.01) | |
| *A61B 17/11* | (2006.01) | |

(52) U.S. Cl.
CPC ..... *A61B 17/06166* (2013.01); *A61B 17/1146* (2013.01); *A61B 2017/00884* (2013.01); *A61B 2017/00951* (2013.01)

(58) Field of Classification Search
CPC .......... A61B 17/06166; A61B 17/1146; A61B 2017/00951; A61B 17/06; A61B 2017/00893; A61B 17/00491; A61B 17/04; A61B 2017/00884; A61B 2017/06185; A61L 17/145
USPC ........................................................ 606/228
See application file for complete search history.

(56) References Cited

U.S. PATENT DOCUMENTS

| | | | |
|---|---|---|---|
| 6,264,675 B1 | 7/2001 | Brotz | |
| 6,478,809 B1 * | 11/2002 | Brotz | ............... A61B 17/00491 606/224 |
| 8,142,475 B2 | 3/2012 | Viola | |
| 9,115,289 B2 * | 8/2015 | Lee | .................... A61L 15/18 |
| 2009/0036611 A1 * | 2/2009 | Wilker | .................. C08F 212/08 525/328.5 |
| 2009/0177228 A1 * | 7/2009 | Aspenberg | ....... A61B 17/06166 606/228 |

OTHER PUBLICATIONS

Jordan Raphel, Andreina Parisi-Amon, and Sarah Heilshorn, Photoreactive elastin-like proteins for use as versatile bioactive materials and surface coatings, (Oct. 7, 2012), NIH Public Access, 1-15 (Year: 2012).*
Bouten et al., "The chemistry of tissue adhesive materials," Progress in Polymer Science, 39, (2014), pp. 1375-1405.
Inoue et al., Effectiveness and biocompatibility of a novel biological adhesive application for repair of meniscal tear on the avascular zone, Sci. Technol. Adv. Mater. 13, (2012) 064219, pp. 1-5.

* cited by examiner

*Primary Examiner* — Christopher L Templeton
*Assistant Examiner* — George J Ulsh
(74) *Attorney, Agent, or Firm* — Armstrong Teasdale LLP

(57) ABSTRACT

The field of the disclosure relates generally to sutures and, more specifically, to enhancing suture repair mechanics using adhesives.

18 Claims, 12 Drawing Sheets

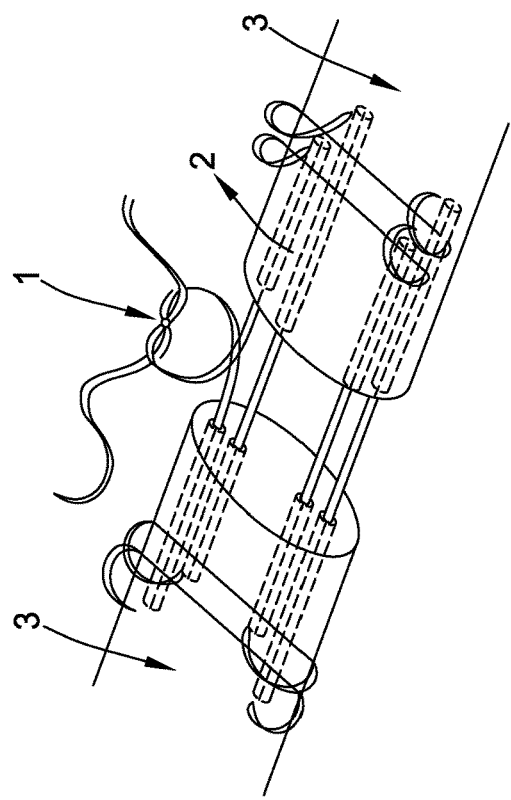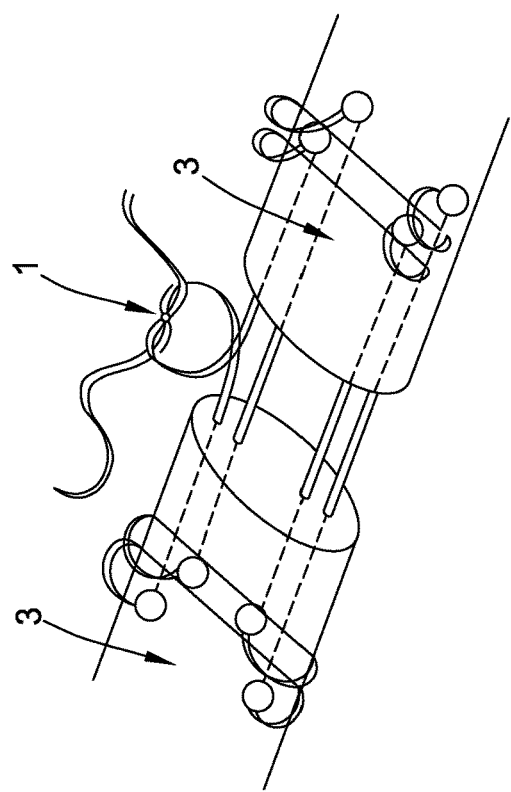

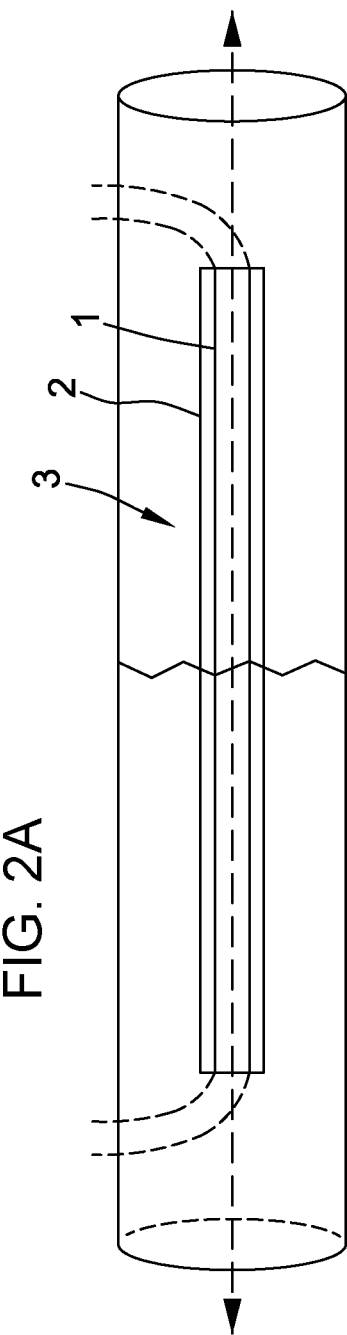
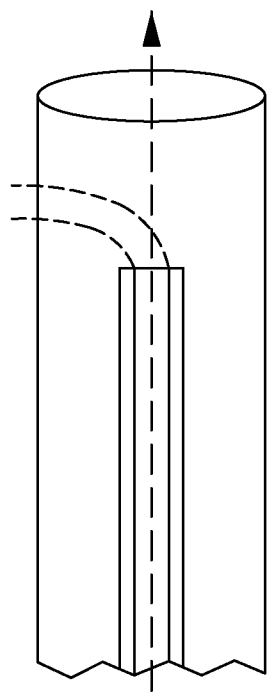
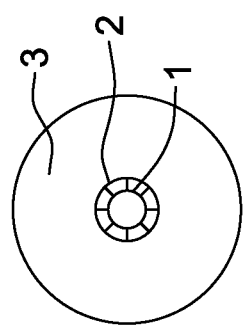
FIG. 2A
FIG. 2B
FIG. 2C

ADHESIVE-COATED SUTURES

CROSS-REFERENCE TO RELATED APPLICATION

This application claims priority to U.S. Provisional Application Ser. No. 62/079,965, filed Nov. 14, 2014, which is incorporated in its entirety.

STATEMENT REGARDING FEDERALLY SPONSORED RESEARCH & DEVELOPMENT

This disclosure was made with government support under grant R01AR062947, awarded by the U.S. National Institutes of Health, grant T32AR060719, awarded by the U.S. National Institutes of Health, and grant T32GM007200, awarded by the U.S. National Institutes of Health. The U.S. government may have certain rights in this disclosure.

BACKGROUND OF THE DISCLOSURE

The field of the disclosure relates generally to sutures and, more specifically, to enhancing suture repair mechanics using adhesives.

While there have been many improvements in suture materials and knot tying techniques since sutures were first used, the core technology of sewing tissues together remains a crude mechanical solution. Sutures are typically in pure tension along most of their length, with this tension transferred to the tissue only at anchor points. High stress concentrations at these anchor points can lead to sutures breaking or cutting through the surrounding tissue, similar to a wire cutting through cheese. This limits the maximum force that can be transferred across the suture repair.

Many surgical repairs, including, but not limited to, orthopaedic repairs (e.g., tendon and ligament repair) demand strong biomechanical resilience to accommodate activities of daily living without risking rupture. For example, repair site elongation and rupture remain problematic after flexor tendon repairs even with modern suturing and rehabilitation protocols. Rotator cuff repairs, which require reattachment of materials with disparate mechanical properties (tendon and bone), have alarmingly high failure rates. Improved suturing schemes would allow for greater loads across the repair site, reducing rupture and gap formation between the repaired tissues.

Traditional sutures transfer load to and from surrounding tissue/material predominantly at anchor points where they bend within the tissue. High stress concentrations at these anchor points can lead to sutures breaking or cutting through the surrounding tissue, similar to a wire cutting through cheese.

This limits the maximum force that can be transferred across the repair. Traditional sutures have a relatively large surface area passing through tissue (or other substrate being sewn together) that is not utilized for load transfer. Thus, a need remains in the art for a modified suture with an adsorbed or covalently bound adhesive that binds collagen along the suture's length, thereby reducing stress concentrations and better distributing load.

BRIEF DESCRIPTION OF THE DISCLOSURE

In one embodiment, an adhesive-coated suture is disclosed.

In another embodiment, a method of surgical repair is disclosed. The method comprises: coating a suture with an adhesive, the coating comprising a protective layer; applying the suture to a part of a body, removing or activating the protective layer, and binding the suture to the part of the body.

BRIEF DESCRIPTION OF THE DRAWINGS

FIG. 1A is an exemplary embodiment of a suture repair technique without an adhesive coating on a suture. FIG. 1B is an exemplary embodiment of a suture repair technique in accordance with the present disclosure.

FIGS. 2A-2C are exemplary embodiments of an adhesive-coated suture assembly in accordance with the present disclosure.

DETAILED DESCRIPTION OF THE DISCLOSURE

As used herein, the term "suture" refers to the core strand of suture; the term "adhesive" refers to the adhesive layer; the terms "assembly" and "adhesive-coated suture" refer to the combination of suture with adhesive surrounding it; and the term "repair" refers to the complete tissue repair, including several strands of adhesive-coated suture used.

The present disclosure is directed to a new approach to suturing technology. Conventional sutures have a relatively large surface area passing through the tendon that is currently not utilized for load transfer. By enabling this surface area to interact mechanically with the surrounding tissue, peak stresses can be reduced at points where the suture bends through tissue (e.g., anchor points). The present disclosure is directed to a modified suture with an adsorbed, ionically bound, or covalently bound adhesive that binds collagen along the suture's length, thereby reducing stress concentrations and better distributing load. This better load distribution improves load tolerance of repaired tendons.

Improved mechanical repair techniques improve patient outcomes by strengthening repairs, thereby decreasing the chance of repair rupture and failure. This disclosure is especially useful and immediately applicable to orthopaedic repairs (e.g., tendon and ligament repair) which demand strong biomechanical resilience to accommodate activities of daily living without risking rupture, though it is also likely useful for other surgical repairs. For example, repair site elongation and rupture remain problematic after flexor tendon repairs even with modern suturing and rehabilitation protocols. Rotator cuff repairs, which require reattachment of materials with disparate mechanical properties (tendon and bone), have alarmingly high failure rates.

Improved suturing schemes would allow for greater loads across the repair site, reducing rupture and gap formation between the repaired tissues. In addition, stronger repairs enable more aggressive rehabilitation protocols, which can have positive effects on the healing process. By holding the tissues together for longer time intervals, mechanical solutions that prevent gap formation could provide more time for the biological healing response to generate a strong, organized tissue instead of disorganized scar.

In some embodiments of the present disclosure, the suture includes an adhesive having properties optimized for load transfer. In other embodiments, the suture includes adhesives having a stiffness that is modified with microstructural features such as, but not limited to, periodic appendages emanating from the suture body. These appendages can serve to further optimize the stiffness and load transfer properties of the adhesive.

Figure 4A:
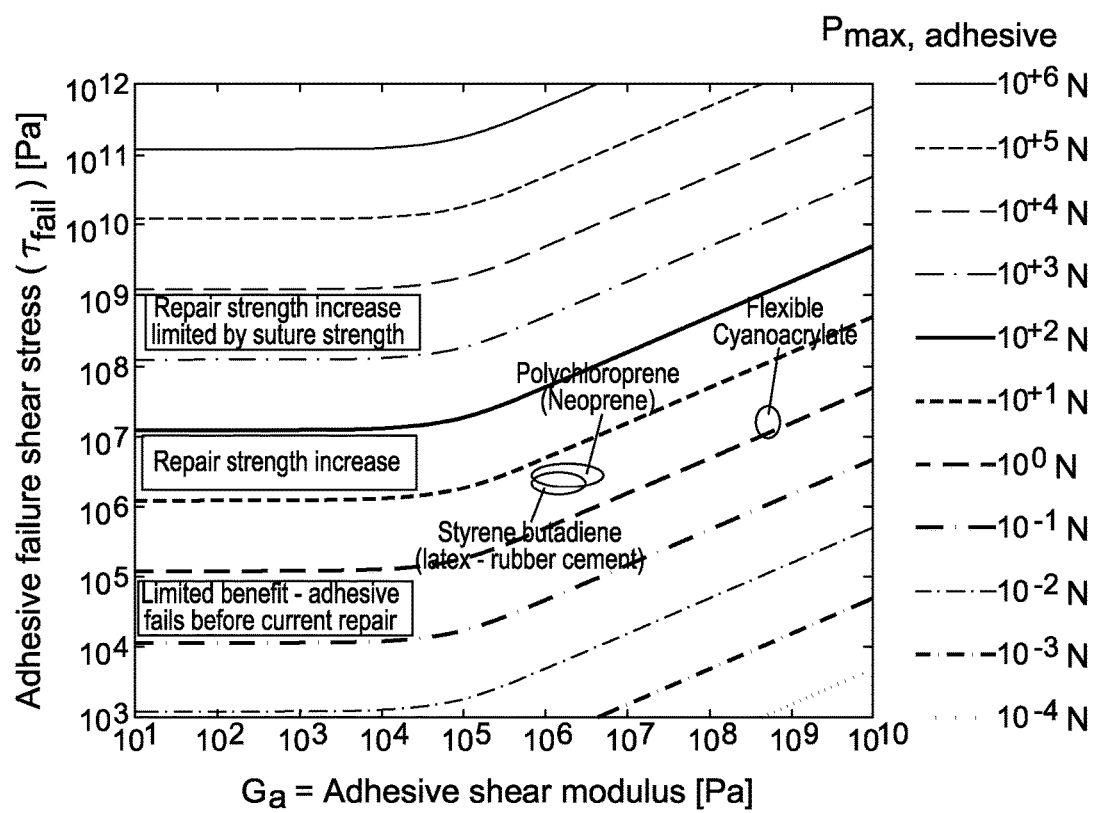
FIGS. 4A and 4B are exemplary embodiments of various loads carried by adhesive-coated sutures in accordance with the present disclosure.
Figure 4B:
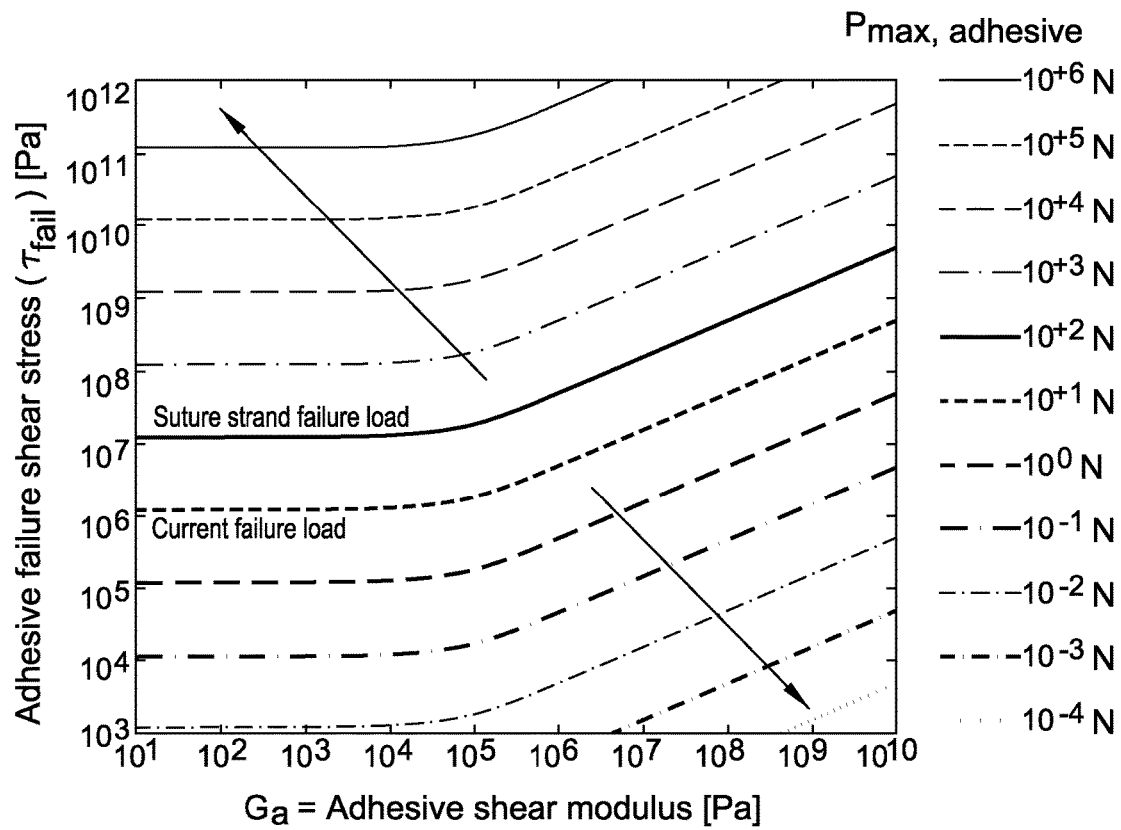

In FIG. 4B, a contour map is shown of maximum load transferred between a single-stranded, adhesive-coated suture within tissue, calculated from a wide array of theoretical adhesive shear moduli and adhesive failure shear stresses (i.e., strengths) given properties described in the models. Maximum theoretical load transfer occurred with an infinitely compliant and infinitely strong adhesive, toward the upper left corner of this contour plot. Current flexor tendon repairs carry approximately 10 N per suture strand, so relevant adhesive coatings would have failure loads around or above this level.

Adhesive mechanical properties that are not expected to improve load transfer are located in the lower portion of the graph, from the $10^6$ failure shear stress toward the $10^{10}$ shear modulus. The suture strand itself breaks above approximately 15.5 N for Supramid 4-0 or 23.5 N for Supramid 3-0 suture, so adhesive failure loads above this level would no longer limit load transfer (upper portion from the $10^7$ shear stress to the $10^{10}$ shear modulus). The shear modulus and failure shear stress are related for a given real material, so not all theoretical combinations are realistic. The adhesive-coated repair strength could be limited by the bulk material properties of an adhesive (overlaid here for several materials tested) or the adhesive binding strength at the tissue interface.

The mechanical properties of suitable adhesives were identified using a mechanical model, such as a shear lag model. Examination of the design space for an optimal adhesive demonstrated a preference for strong adhesion and compliant stiffness to maximize the strength of the adhesive-coated suture repair construct. As a proof of concept, cyanoacrylate-coated sutures were used to perform a clinically relevant flexor digitorum tendon repair in cadaver tissue. The repair performed with adhesive-coated suture had significantly higher strength compared to the standard repair without adhesive. Notably, cyanoacrylate provides strong adhesion with high stiffness and brittle behavior, and is therefore not an ideal adhesive for enhancing suture repair. Nevertheless, the improvement in repair properties in a clinically relevant setting, using a non-ideal adhesive, demonstrates the potential for this approach to improve outcomes for treatments requiring suture fixation. The present disclosure is further directed to a strongly adherent, compliant adhesive within the optimal design space described by the shear lag model.

Sutures are an age-old technology and have been used for wound repair for years. While there have been many improvements in suture materials and intricate knot tying techniques, the core technology of simply sewing tissues together remains a crude mechanical solution. Sutures are typically in pure tension along most of their length, with this tension transferred to the tissue only at anchor points (shown in FIG. 1A). High stress concentrations at these anchor points can lead to sutures breaking or cutting through the surrounding tissue, similar to a wire cutting through cheese. This limits the maximum force that can be transferred across the repair. While current suturing techniques are sufficient to hold many surgical repairs together, musculoskeletal repairs (e.g., tendon and ligament repair) typically demand strong biomechanical resilience to accommodate activities of daily living without risking rupture. For example, repair site elongation and rupture remain problematic after flexor tendon repairs even with modern suturing and rehabilitation protocols. Rotator cuff repairs, which require reattachment of materials with disparate mechanical properties (tendon and bone), have alarmingly high failure rates. Improved suturing schemes would allow for greater loads across the repair site, reducing rupture and gap formation between the repaired tissues and improving healing outcomes.

The present disclosure is directed to a new approach to augment standard suturing technology. Conventional sutures have a relatively large surface area passing through the tendon that is currently not utilized for load transfer. This improvement in load transfer results in an improvement in overall repair construct mechanical properties. In order to predict the ability of adhesive-coated sutures to improve load transfer, a shear lag model of suture within a cylindrical tissue (e.g., a tendon) was developed. Using this model, desirable adhesive mechanical properties were identified to improve load transfer across a repair site. Biomechanical tests with suture coated adhesives were conducted to validate the model and experimentally assess the ability to improve load transfer.

A mechanical model, such as a shear lag model, to determine stresses along an adhesive-coated suture's length, which allows one to predict the maximum amount of load that an adhesive-coated suture could transfer between two sides of a repair can be used in certain embodiments of the present disclosure. This maximum load is a function of adhesive, tissue, and suture material and geometrical properties. This allows one to plot isoclines for the amount of load transferred on a domain map of theoretical adhesive mechanical properties, specifically, shear modulus ($G_a$) vs. failure shear stress ($\tau_{fail}$). Therefore, this domain map of adhesive mechanical properties shows the desirable adhesive properties needed to improve load transferred across suture-based repairs. Engineering and biological materials can be overlaid on this plot to determine which materials might be suitable adhesives, and to determine which materials might be useful potential components to design a suitable adhesive. This modeling showed that ideal adhesives are thick layers, compliant to shear, yet still strong in shear (i.e., high failure shear stress). Therefore, this modeling can be used to intelligently and intentionally develop adhesive-coated sutures to optimize load transfer.

To experimentally assess the ability to improve load transfer, adhesive coatings were biomechanically tested on single suture strands within tendon tissue. Loctite 4903, a "flexible" cyanoacrylate, improved the maximum load to pull out a single suture strand in tendon from 0.076 N (+/−0.104 N standard deviation) without adhesive to 3.24 N (+/−2.11 N) with an adhesive-coated suture strand. In a full, 8-stranded cadaveric canine flexor tendon repair, cyanoacrylate-coated sutures increased maximum load transfer by 17.0% (Control=72.7+/−11.3 N; Loctite 4903=85.0+/−8.6 N; p=0.009) and load to create a clinically relevant 2 mm gap by 17.5% (Control=59.1+/−8.8 N; Loctite 4903=69.5+/−11.2 N; p=0.029) compared to standard 8-stranded suture repairs without adhesive-coatings.

In some embodiments, Loctite 4903 shows promising results that would be valuable clinically. Adhesives with optimized mechanical and chemical properties were developed to further increase load transfer and improve clinical repairs for tendon, ligament, and other tissue injuries, as an initial application of the technology. These adhesives are specifically designed to meet the compliant yet strong criteria and can enable substantially stronger suture repairs.

The present disclosure is directed to novel adhesive technologies that apply existing or novel adhesives in a novel way and/or apply novel structural methods to modify the stiffness of an adhesive layer. The present disclosure is also directed to a protein-based bioadhesive with desirable mechanical properties by using a suture-binding domain linked to a compliant domain, which can be linked in series to a tissue-binding domain. For instance, by way of non-limiting examples, a silk-binding domain could be used for binding silk sutures, an elastin moiety or a protein sequence with similar mechanical properties could provide the desired compliance properties, and a collagen-binding sequence such as an integrin could be used to specifically bind the surrounding tissue.

Silk-HRP Gels (silk hydrogels cross-linked with $H_2O_2$ in the presence of horseradish peroxidase) represent an attractive bulk adhesive material for use with sutures because they are biocompatible, degradable, and have tunable mechanical properties.

In addition to mechanical properties, for surgical ease of use, in some embodiments ideal adhesives are not "sticky" or activated until they are implanted and in their final location. Therefore, the present disclosure is directed to various protective mechanisms to only activate the adhesive when appropriate. This can be done in several ways. The present disclosure is also directed to coating adhesives in a protective layer that melts away based on either temperature or an activating stimulus such as near infrared radiation. Once the protective layer is melted or removed, the adhesive would be uncovered for binding the surrounding tissue material.

FIGS. 1A and 1B include diagrams illustrating example suture repair techniques including a typical suture repair and an example adhesive-coated suture repair. This system can also be seen in FIGS. 2A-2C. The typical suture repair is an 8-stranded Winters-Gelberman suture repair technique for human flexor digitorum profundus tendon repair. Some known suturing techniques generate stress concentrations at anchor points where the suture bends within tissue. The adhesive-coated suture repair enables distributing that load transfer along the entire length of the suture, reducing peak stresses and enhancing overall repair construct mechanics. As shown in FIGS. 1A and 1B, a suture 1 is used to repair a tendon 3. The technique shown in FIG. 1A is a conventional technique, while the technique shown in FIG. 1B is in accordance with the present disclosure wherein the suture 1 is coated with an adhesive 2 and used to repair the tendon 3.

FIGS. 2A-2C include diagrams illustrating another example adhesive-coated suture assembly within a cylindrical tissue (e.g., tendon) used to derive shear lag analysis. $P_s$ is the tensile load carried by the suture at the interface between repaired tissues (i.e., at x=0). $P_k$ is the load at an anchor point or knot, where the suture bends within the tissue (i.e., at x=L). This load, when too high, leads to the assembly cutting through surrounding tissue and to rupture of the repair.

As an example of an analysis to identify adhesives with desirable properties for suture repair, a shear lag model was developed to predict the load sharing between the sutures and a repaired tendon by estimating the variation of the shear stress in the adhesive layer, τ, as a function of the position, x, along a suture, as diagrammed in FIGS. 2A-2C:

$$\frac{\tau}{\bar{\tau}} = \frac{\lambda_s L}{\xi \sinh(\lambda_s L)} \left\{ (\xi - 1)\cosh(\lambda_s(x - L)) - \left(\frac{P_k}{P_s}\xi - 1\right)\cosh(\lambda_s x) \right\}$$

where $\bar{\tau}$ is the average shear stress; L is the suture length; $P_k$ is the load in the suture at the anchor point (i.e., at the knot, at distance L along the tendon); and $P_s$ is the load in the suture at the interface (i.e., x=0). ξ and $\lambda_s$ relate to the geometry and material properties:

$$\xi \equiv 1 + \frac{E_t(r_t^2 - (r_s + t_a)^2)}{E_s r_s^2} \approx 1 + \frac{E_t r_t^2}{E_s r_s^2}$$

$$\lambda_s^2 \equiv \frac{2G_a}{t_a}\left(\frac{r_s}{E_t(r_t^2 - (r_s + t_a)^2)} + \frac{1}{r_s E_s}\right)$$

where $G_a$ is the adhesive shear modulus, $t_a$ is the adhesive thickness, $r_t$ is the tendon radius, $r_s$ is the suture radius, and $E_t$ and $E_s$ are tendon and suture Young's modulus, respectively.

This model's derivation (shown in detail, below) and final form are directly analogous to the Volkersen and Cox shear lag solutions for double lap joints. Unlike the Volkersen and Cox derivation, however, this model includes an extra term, $P_k$, since the pressure at the anchor point where the suture begins to bend is not necessarily zero. Other terms are modified from these prior solutions to take into account a cylindrical geometry rather than a rectangular geometry. This derivation is consistent with other known cylindrical shear lag derivations.

In deriving the shear lag model, derivation of the example model follows shear lag solution for a double lap joint. A free body diagram of the adhesive suture model system can also be used.

FIGS. 2A-2C include a free body diagram showing a two-dimensional axisymmetric model of adhesive-coated suture within a cylindrical tendon tissue (top, FIG. 2A). Simultaneously analyzing a section of the repair (bottom left, FIG. 2B) and each component independently (i.e., suture, adhesive, and tendon; bottom right, FIG. 2C) allows derivation of a shear lag model to estimate shear stress within the adhesive. The example model reduces to a one-dimensional set of equations along the x-axis.

To estimate the load that would cause adhesive failure, the variation of shear stress, τ(x), at position x was determined as a function load in the suture, P(x). This calculated shear stress was compared to the failure shear stress, $\tau_{fail}$, which could be limited by failure in the bulk of the adhesive, failure at the interfaces with adherends (i.e., suture or surrounding tissue), or failure within the adherends themselves. Strength of materials estimates provided an average shear stress value, $\bar{\tau}$:

$$\bar{\tau} = \frac{P_s}{2\pi r_s L} \quad (1.1.)$$

where $P_s$ is the load in the suture at the interface (position x=0), $r_s$ is the suture radius, and L is the suture length.

Shear stress as a function of position was determined from equilibrium equations, constitutive equations, and strain-displacement equations for the elements in the free body diagram (shown in FIGS. 2A-2C). Equilibrium equations for a section of the repair, the suture (inner adherend), and tendon (outer adherend), were applied:

$$P_s = \pi r_s^2 \sigma_s + \underbrace{\pi(r_t^2 - (r_s + t_a)^2)}_{=r_t^{*2}}\sigma_t \quad (1.2.)$$

$$\frac{d\sigma_s}{dx} = \frac{-2\tau}{r_s} \quad (1.3.)$$

$$\frac{d\sigma_t}{dx} = \frac{2(r_s + t_a)\tau}{r_t^2 - (r_s + t_a)^2} \quad (1.4.)$$

where $\sigma_s(x)$ and $\sigma_t(x)$ are suture and tendon normal stresses at position x, respectively (assumed to not vary with radius r), $r_t$ is the tendon radius, $t_a$ is the adhesive thickness, and $r_t^*$ relates geometric properties.

Constitutive and strain-displacement equations were also applied:

Constitutive Equations:

$$\epsilon_t = \frac{\sigma_t}{E_t} \quad (1.5.)$$

$$\gamma_a = \frac{\tau}{G_a} \quad (1.6.)$$

$$\epsilon_s = \frac{\sigma_s}{E_s} \quad (1.7.)$$

Strain-Displacement Equations:

$$\epsilon_t = \frac{\partial u_t}{\partial x} = \frac{du_t}{dx} \text{ (since this is a 1D problem)} \quad (1.8.)$$

$$\gamma_a = \frac{u_t - u_s}{t_a} \quad (1.9.)$$

$$\epsilon_s = \frac{\partial u_s}{\partial x} = \frac{du_s}{dx} \text{ (since this is a 1D problem)} \quad (1.10.)$$

where $\epsilon_s(x)$ and $\epsilon_t(x)$ are suture and tendon normal strains at position x, respectively (assumed to not vary with radius r), $\gamma_a(x)$ is adhesive shear strain at position x, $E_s$ and $E_t$ are suture and tendon Young's moduli, respectively, $G_a$ is adhesive shear modulus, and $u_s(x)$ and $u_t(x)$ are suture and tendon displacement in the x direction at position x, respectively. Note that this derivation neglects adhesive deformation and neglects normal stresses transferred in the adhesive layer.

The equilibrium, constitutive, and strain-displacement equations combine to yield a second order differential equation for normal stress in the suture:

$$\frac{d^2\sigma_s}{dx^2} - \lambda_s^2 \sigma_s + C_s = 0 \quad (1.11.)$$

where $\lambda_s$ and $C_s$ relate to the geometry and material properties:

$$\lambda_s^2 \equiv \frac{2G_a}{t_a}\left(\frac{r_s}{E_t(r_t^2 - (r_s + t_a)^2)} + \frac{1}{r_s E_s}\right) \quad (1.12.)$$

$$C_s \equiv \frac{2G_a}{t_a}\left(\frac{P_s}{r_s E_t \pi(r_t^2 - (r_s + t_a)^2)}\right) \quad (1.13.)$$

To solve the second order differential equation for normal stress in the suture (1.11), boundary conditions for normal stress in the suture were applied:

$$\iint_0^A \sigma_s(r,x)dA = \int_0^{2\pi}\int_0^{r_s}\sigma_s(r,x)rdr\,d\theta = 2\pi\int_0^{r_s}\sigma_s(r,x)rdr]_{x=0} = P(x) \quad (1.14.)$$

where A is the cross sectional area of the suture.

Assuming normal stress does not vary with radius r, $$P(x) = 2\pi\int_0^{r_s}\sigma_s(x)rdr = \pi r_s^2 \sigma_s(x) \quad (1.15.)$$

$P_s$ is defined as the load in the suture at the interface (position x=0) and $P_k$ is defined as the load in the suture at the anchor point or knot (distance L into the tendon).

The boundary conditions reduce to:

$$\sigma_s(0) = \frac{P_s}{\pi r_s^2} \quad (1.16.)$$

$$\sigma_s(L) = \frac{P_k}{\pi r_s^2} \quad (1.17.)$$

These boundary conditions can then be applied to solve for the normal stress in the suture:

$$\sigma_s(x) = \left(\frac{P_s}{\pi r_s^2} - \frac{C_s}{\lambda_s^2}\right)\cosh(\lambda_s x) + \quad (1.18.)$$

$$\frac{\sinh(\lambda_s x)}{\sinh(\lambda_s L)}\left(\frac{P_k}{\pi r_s^2} - \frac{C_s}{\lambda_s^2} + \left(\frac{C_s}{\lambda_s^2} - \frac{P_s}{\pi r_s^2}\right)\cosh(\lambda_s L)\right) + \frac{C_s}{\lambda_s^2}$$

Shear stress τ(x) at position x can be determined by taking the derivative of normal stress in the suture with respect to position x and applied to the equilibrium equation for the suture (inner adherend, 1.3):

$$\tau = \quad (1.19.)$$

$$\frac{r_s \lambda_s}{2\sinh(\lambda_s L)}\left\{\left(\frac{P_s}{\pi r_s^2} - \frac{C_s}{\lambda_s^2}\right)\cosh(\lambda_s(x-L)) - \left(\frac{P_k}{\pi r_s^2} - \frac{C_s}{\lambda_s^2}\right)\cosh(\lambda_s x)\right\}$$

This shear stress can then be normalized by the average shear stress from the strength of materials solution (1.1) to yield an analogous relationship to the shear lag solution for a double lap joint:

$$\boxed{\frac{\tau}{\bar{\tau}} = \frac{\lambda_s L}{\xi \sinh(\lambda_s L)}\left\{(\xi - 1)\cosh(\lambda_s(x-L)) - \left(\frac{P_k}{P_s}\xi - 1\right)\cosh(\lambda_s x)\right\}} \quad (1.20.)$$

where ξ relates to the geometry and material properties:

$$\xi \equiv 1 + \frac{E_t(r_t^2 - (r_s + t_a)^2)}{E_s r_s^2} \approx 1 + \frac{E_t r_t^2}{E_s r_s^2} \quad (1.21.)$$

Note that peak stress is minimized if the inner and outer adherends are "balanced" by:

$$E_s r_s^2 = E_t(r_t^2 - (r_s + t_a)^2) = E_t r_t^{*2} \approx E_t r_t^2 \text{ (if } r_t >> r_s + t_a) \quad (1.22.)$$

These adherends are not balanced with current Supramid surgical suture and tendon. When adherends (tendon and suture) are balanced by assuming 38× stiffer suture, the peak stress is 8.5 fold lower (assuming geometry and material properties used in FIG. 3B).

The shear lag relationship (1.20) can be rearranged to solve for the load transferred across the interface:

$$P_s = 2\pi r_s L \tau \frac{\sinh(\lambda_s L)}{\lambda_s L} \frac{\xi}{(\xi - 1)\cosh(\lambda_s(x - L)) - \left(\frac{P_k}{P_s}\xi - 1\right)\cosh(\lambda_s x)} \quad (1.23.)$$

Figures 3A, 3C:
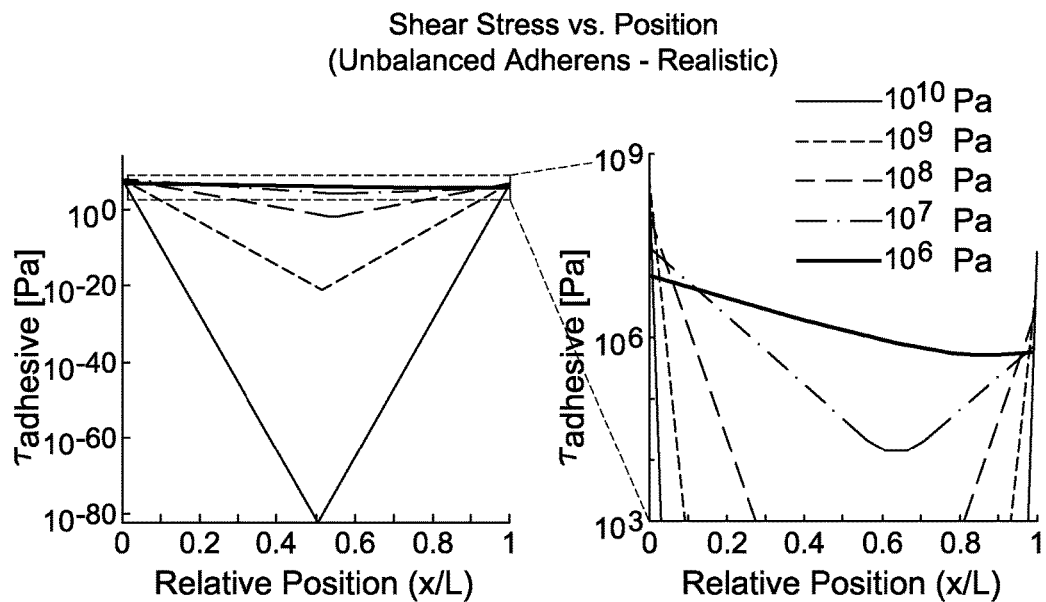
FIGS. 3A-3D are exemplary embodiments of the shear stress vs. position along the length of a suture in accordance with the present disclosure.

Note that shear stress in the adhesive is highest at the interface (x=0, FIG. 3A). Therefore, shear stress at position x=0 is the limiting factor that causes the adhesive to fail. The calculated shear stress was equated to the failure shear stress, $\tau_{fail}$, to determine the amount of load that the adhesive-coated suture could bear before failure, in the case where $P_k=0$:

$$\boxed{P_{max} = 2\pi r_s L \tau_{fail} \frac{\sinh(\lambda_s L)}{\lambda_s L} \frac{\xi}{[(\xi - 1)\cosh(-\lambda_s L) + 1]}} \quad (1.24.)$$

The maximum load transferred by an adhesive-coated suture strand is governed by two asymptotes:

$$\lim_{G_a \to 0} P_{max} = 2\pi r_s L \tau_{fail} L \quad (1.25.)$$

$$\lim_{L \to \infty} P_{max} = 2\pi r_s \tau_{fail} (\lambda_s)^{-1} * \frac{\xi}{(\xi - 1)} \quad (1.26.)$$

$$= 2\pi r_s \tau_{fail} \left(\frac{t_a}{2G_a r_s}\left(\frac{E_s r_s^2}{E_t r_t^{*2}}\right)(E_s r_s^2 + E_t r_t^{*2})\right)^{+\frac{1}{2}}$$

These two asymptotes intersect at suture length $L_{intersect}$ (shown in FIGS. 5A and 5B):

$$L_{intersect} = \left[\frac{t_a}{2G_a r_s}\left(\frac{E_s r_s^2}{2G_a r_s^2}\right)(E_s r_s^2 + E_t r_t^{*2})\right]^{\frac{1}{2}} \quad (1.27.)$$

Figures 3B, 3D:
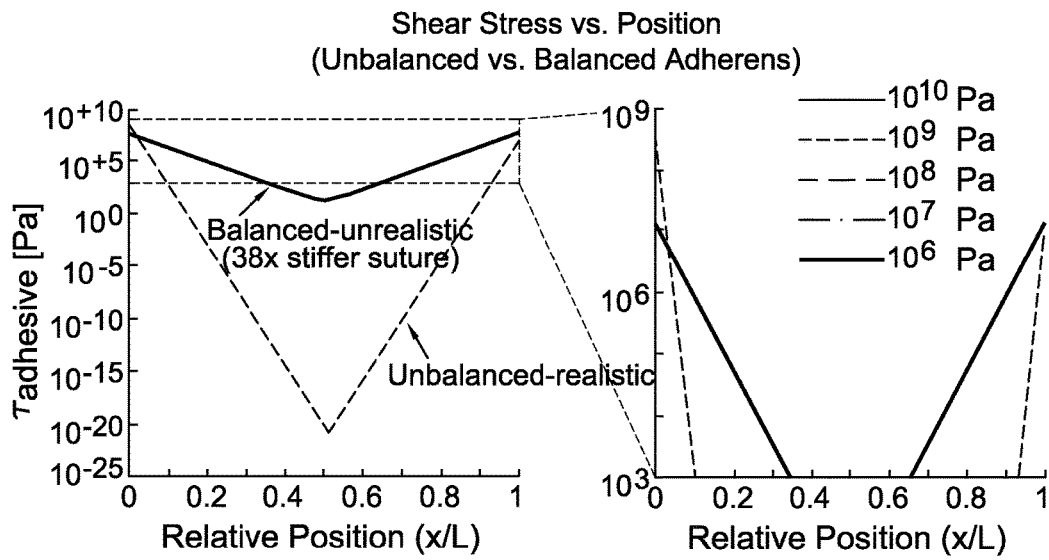

FIGS. 3A-3D include diagrams illustrating shear stress vs. position along the length of a suture. As shown in FIG. 3A and zoomed version (FIG. 3C), comparing adhesive shear moduli for realistic suture and tendon properties demonstrates that more compliant adhesives have a lower peak shear stress since compliant adhesives distribute loads over a longer distance than stiffer adhesives. As shown in FIG. 3B and zoomed version (FIG. 3D), realistic parameter values described in the methods produce unbalanced adherends (tendon and suture) (yellow line, $G_a=1$ GPa), leading to substantially higher peak stresses. When adherends are balanced (i.e., $E_t r_t^{*2} = E_s r_s^2$) by assuming 38× stiffer suture (blue line, $G_a=1$ GPa), the peak stress is 8.5 fold lower than for unbalanced adherends. These calculations set $P_k$ to 0N, so all of the load carried by the suture is transferred to the surrounding tissue via the adhesive.

Note that the shear stress in the adhesive is highest at position x=0 (i.e., the tendon-tendon repair interface; shown in FIG. 3A). Solving for maximum transferable load across the repaired interface, $P_{max}$, considering position x=0 and load $P_k=0$:

$$P_{max} = 2\pi r_s L \tau_{fail} \frac{\sinh(\lambda_s L)}{\lambda_s L} \frac{\xi}{[(\xi - 1)\cosh(-\lambda_s L) + 1]}$$

where $\tau_{fail}$ is the failure shear stress of the adhesive.

The maximum transferable load is governed by two asymptotic limits:

$$\lim_{G_a \to 0} P_{max} = 2\pi r_s L \tau_{fail}$$

$$\lim_{L \to \infty} P_{max} = 2\pi r_s \tau_{fail} \left(\frac{t_a}{2G_a r_s}\left(\frac{E_s r_s^2}{E_t r_t^{*2}}\right)(E_s r_s^2 + E_t r_t^{*2})\right)^{+\frac{1}{2}}$$

Note that these limits allow prediction of desirable adhesive and suture properties. The asymptotic limits intersect at suture length:

$$L_{intersect} = \left[\frac{t_a}{2G_a r_s}\left(\frac{E_s r_s^2}{E_t r_t^{*2}}\right)(E_s r_s^2 + E_t r_t^{*2})\right]^{\frac{1}{2}}$$

As a test case for a clinically relevant suture repair scenario, the model was analyzed using realistic tendon and suture material properties and a variety of realistic suture lengths and adhesive properties for a typical flexor digitorum profundus clinical repair: L=13 mm, $r_t=2$ mm, $E_t=200$ MPa, $t_a=100$ μm, $r_s=100$ μm, and $E_s=2$ GPa.

To experimentally assess the ability of adhesives to improve load transfer, various adhesive coatings were added to single suture strands and inserted into tendon tissue prior to preforming pullout tests. The following adhesives were examined: high flex cyanoacrylates (Loctite 4903 and 4902; Henkel Corporation, Düsseldorf, Germany), rubber cement (Elmer's Rubber Cement; Elmer's Products, Inc., Columbus, Ohio), and rubber/gasket adhesive (1300 Scotch-Weld Neoprene High Performance Rubber & Gasket Adhesive; 3M, St. Paul, Minn.). Loctite 4903 and 4902 have shear moduli of 538 MPa and 399 MPa, respectively. Rubber cement and rubber/gasket adhesives have shear moduli between about 0.5 to 5 MPa. Polyfilament caprolactam 4-0 suture (Supramid, S. Jackson, Inc., Alexandria, Va.) was passed through cadaveric canine hindpaw flexor digitorum profundus tendons using a French eye needle (canine tissues were taken post-mortem from an unrelated project). The tendon was first dissected away from surrounding tissue and a complete laceration was made in Zone II perpendicular to the tendon. Suture was passed from the side of the tendon about 8 to 12 mm from the laceration interface toward the laceration interface, and the suture was pulled through the tendon so only a single suture strand remained within the tendon. In adhesive-coated tests, adhesive was then injected onto the suture and the suture was pulled into place, dragging the adhesive into the tendon. Adhesive that accumulated on the side of the tendon was immediately cleaned off with gauze soaked in phosphate buffered saline (PBS). The assembly within the tendon was wrapped in PBS-soaked gauze in an airtight tube and then allowed to cure overnight at 4° C. before biomechanical testing or histological assessment.

To further assess the ability of adhesive to improve load transfer in a clinically relevant setting, cadaveric canine hindpaw flexor digitorum profundus tendons with Zone II lacerations were repaired using an 8-strand Winters-Gelberman repair (N=11) (Supramid 4-0 suture; S. Jackson Inc., Alexandria, Va.), as shown in FIGS. 1A and 1B. Control repairs without adhesive were compared to repairs with Loctite 4903-coated suture. Loctite 4903 was chosen based on results of single suture pullout tests described above. For adhesive-augmented repairs, sutures were passed through the tendon following usual surgical technique, then for each suture pass, Loctite 4903 was injected onto the suture strands using a syringe immediately prior to pulling the adhesive-coated suture into its final position. The outside of the tendon was thoroughly cleaned with PBS-soaked gauze to remove any excess adhesive. Repairs were completed with a continuous, nonlocking peripheral stitch using 5-0 nylon suture, as performed clinically. The repaired tendon and distal phalangeal bone were wrapped in PBS-soaked gauze in an airtight tube and then allowed to cure overnight at 4° C. before biomechanical testing.

Biomechanical testing was conducted for sample sutures. Samples were brought to 37° C. prior to biomechanical testing. For single suture strand pullout tests, any suture and adhesive outside of the lateral tendon was first removed. Samples were then tested in uniaxial tension on a materials testing frame (ElectroPuls E1000; Instron Corp., Candon, Mass.) at 0.3 mm/s. The length of exposed tendon was approximately 15.0 mm for all samples, and the gauge length between the tendon and suture grips was 8.5 cm for all samples. Pullout (or failure) force of single adhesive-coated suture strands within tendon tissue were determined from the force-elongation curves.

Additional testing was conducted for clinical repairs of cadaveric flexor digitorum profundus tendons. Samples were preconditioned and pulled in uniaxial tension using a material testing machine (5866; Instron Corp., Norwood, Mass.) at 0.3 mm/s until failure. Strain was determined optically. From the force-elongation curves, maximum force, force required to create a 2 mm gap in the repair (a clinically relevant measure of repair strength), and stiffness (slope of the linear region) were determined. From the force-strain curves, strain at 20 N force (approximating strains at physiologically relevant load levels) and resilience (area under the curve until yield) were determined.

Figure 5A:
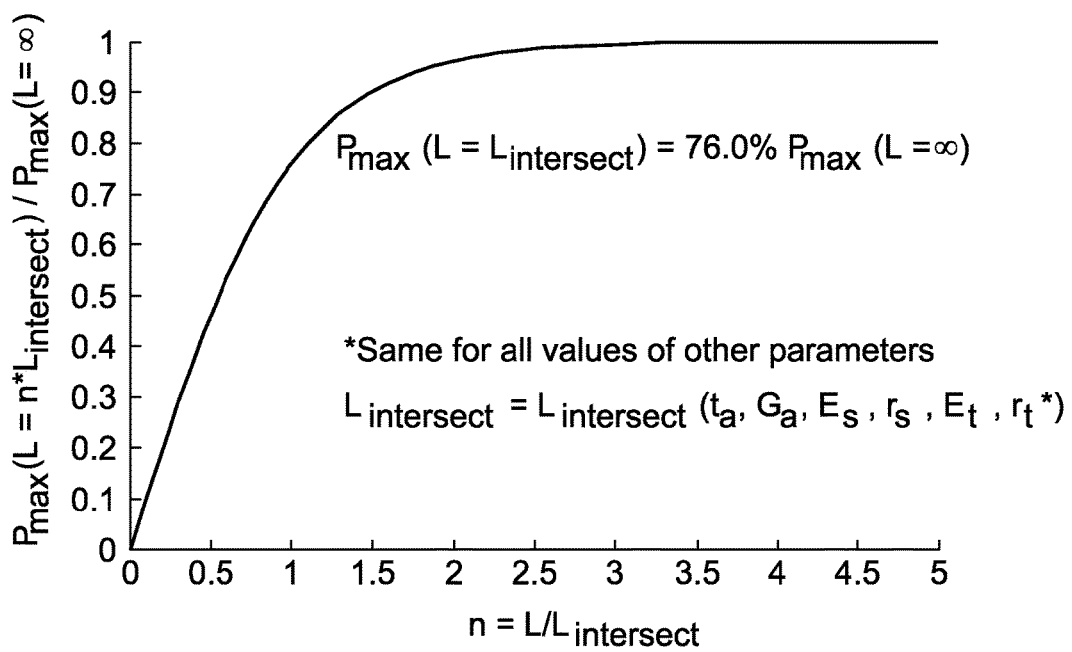
FIG. 5A is an exemplary embodiment of a graphical depiction of suture load in accordance with the present disclosure.
Figure 5B:
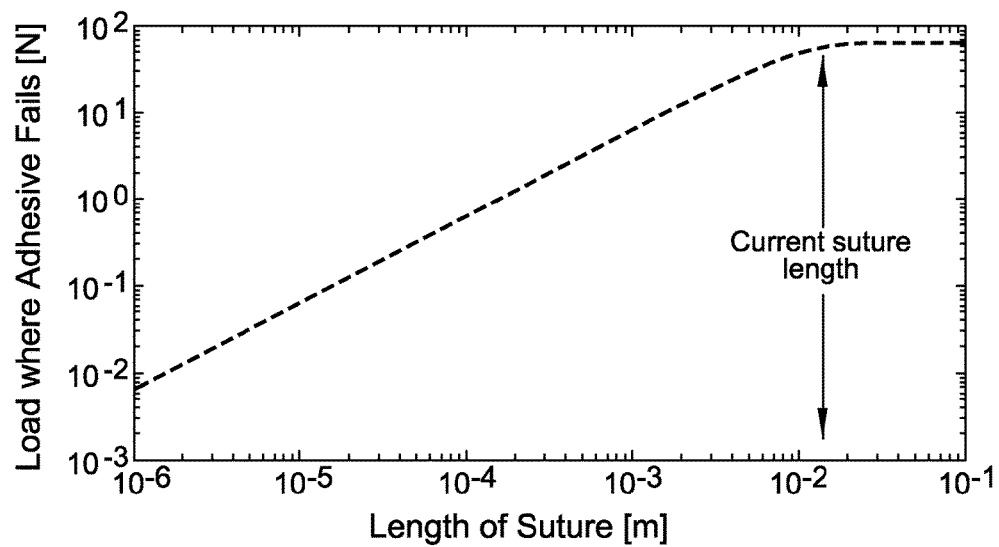
FIG. 5B is an exemplary embodiment of a graphical depiction of suture load carried by assembly vs. length in accordance with the present disclosure.

Shear lag model analysis of example adhesive coating sutures was conducted. FIGS. 4A, 5A, and 5B illustrate results of shear lag model analysis of example adhesive coating sutures.

FIG. 4A includes a contour map illustrating maximum load transferred across the repair by an adhesive-coated suture, calculated from a wide array of theoretical adhesive shear moduli and adhesive failure shear stresses (i.e., strengths) given properties described in the methods. Maximum load transfer occurred with an infinitely compliant and infinitely strong adhesive, toward the upper left corner of this contour plot. Current flexor tendon repairs carry approximately 10 N per suture strand, so relevant adhesive coatings would have failure loads above this level. Adhesive mechanical properties that do not improve load transfer are located, for example, in the lower portion of FIG. 4A. Note that the suture strand itself breaks above approximately 15.5 N for Supramid 4-0 or 23.5 N for Supramid 3-0 suture, so adhesive failure loads above this level would not further improve load transfer (located, for example, in the upper portion). Note that shear modulus and failure shear stress are related for a given real material, so not all theoretical combinations are realistic.

FIGS. 5A and 5B include diagrams illustrating increasing suture length increases maximum load carried by assembly, i.e., load causing adhesive to fail, only until a point. Above a transitional suture length, load capacity is governed by an asymptote independent of suture length. Note that axes are logarithmic scale. Current suture length used in flexor tendon repair is 12 mm into each tendon end.

Referring to FIGS. 4A, 5A, and 5B, shear lag modeling predicted that adhesive coatings on sutures would improve load transfer compared to conventional sutures for a certain range of properties (in between $10^6$ and $10^7$ shear stress as shown in FIG. 4A). Mechanically desirable adhesives would be compliant in shear while maintaining high binding and shear strengths. Compliant adhesives allow greater deformation, thereby distributing loads over a larger length than stiff adhesives (shown in FIG. 3A). This distribution reduces stress concentrations at the suture anchor points, leading to an adhesive-coated suture assembly that carries greater load before failure. In addition to adhesive properties, the maximum shear stress in the adhesive is minimized by balancing the adherends (i.e., tissue and suture) according such that $E_s r_s^2 = E_t (r_t^2 - (r_s + t_a)^2)$. These adherends are not balanced with current Supramid surgical suture and tendon. When adherends (tendon and suture) are balanced by assuming 38× stiffer suture, the peak stress is 8.5 fold lower (shown in FIG. 3B).

Shear lag modeling also predicted that maximum load transfer would increase with increasing adhesive-coated suture length. However, varying the ratio of suture length to $L_{intersect}$ demonstrates that adhesive-coated sutures approach the limit for maximum load transferred when the suture length, L, is about 2 to 3 times $L_{intersect}$ (shown in FIG. 5A). The length of suture used is limited surgically by the particular tissue being repaired. Suture length of 13 mm was used in the model to make results relevant to flexor digitorum profundus tendon repair (shown in FIG. 5B). A contour map of maximum load transfer given various adhesive properties was generated using this length (shown in FIG. 4A). Properties of several real materials were then overlaid on this contour map to identify promising candidate materials. Assuming a compliant adhesive ($G_a$=100 kPa) with a strong shear strength ($\tau$=10 MPa) and the current clinical suture length of 13 mm, maximum load transfer per strand would approach 70 N of force.

Figure 6:
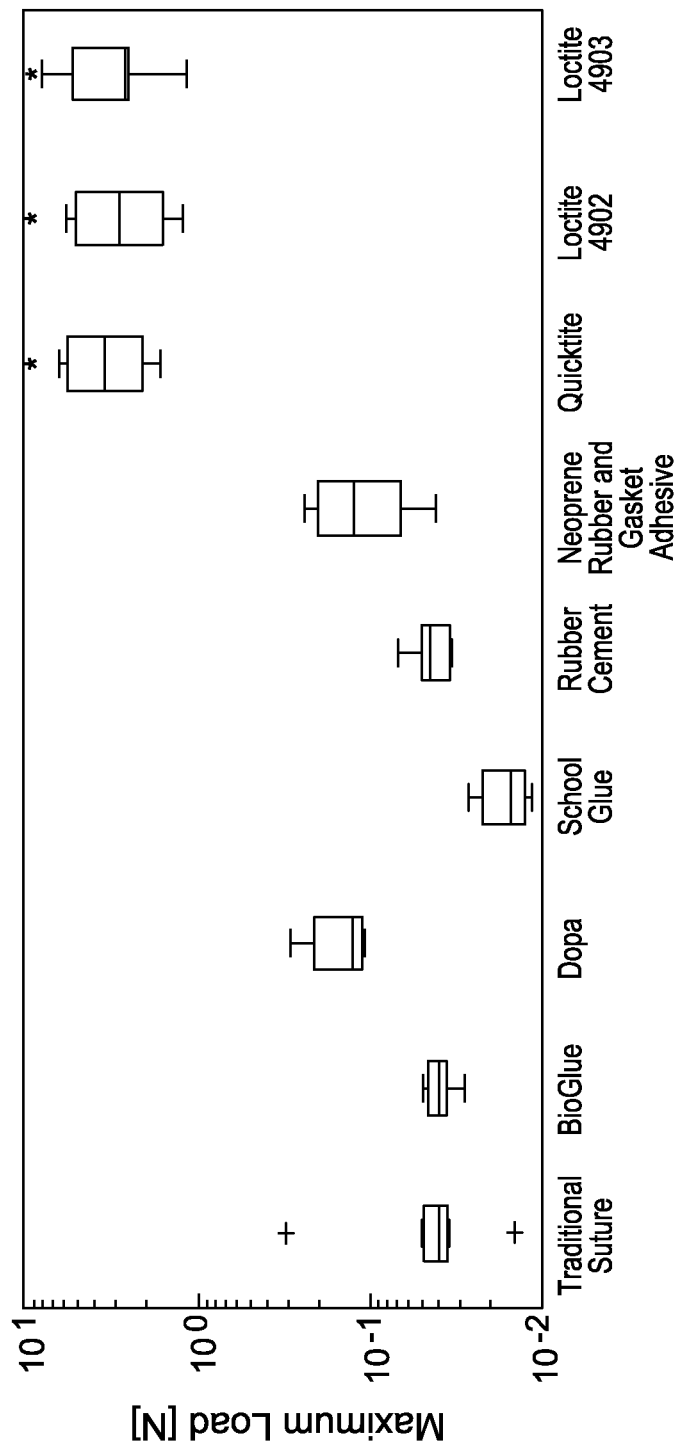
FIG. 6 is an exemplary embodiment of maximum loads resisted by single suture strands in accordance with the present disclosure.
Figure 7:
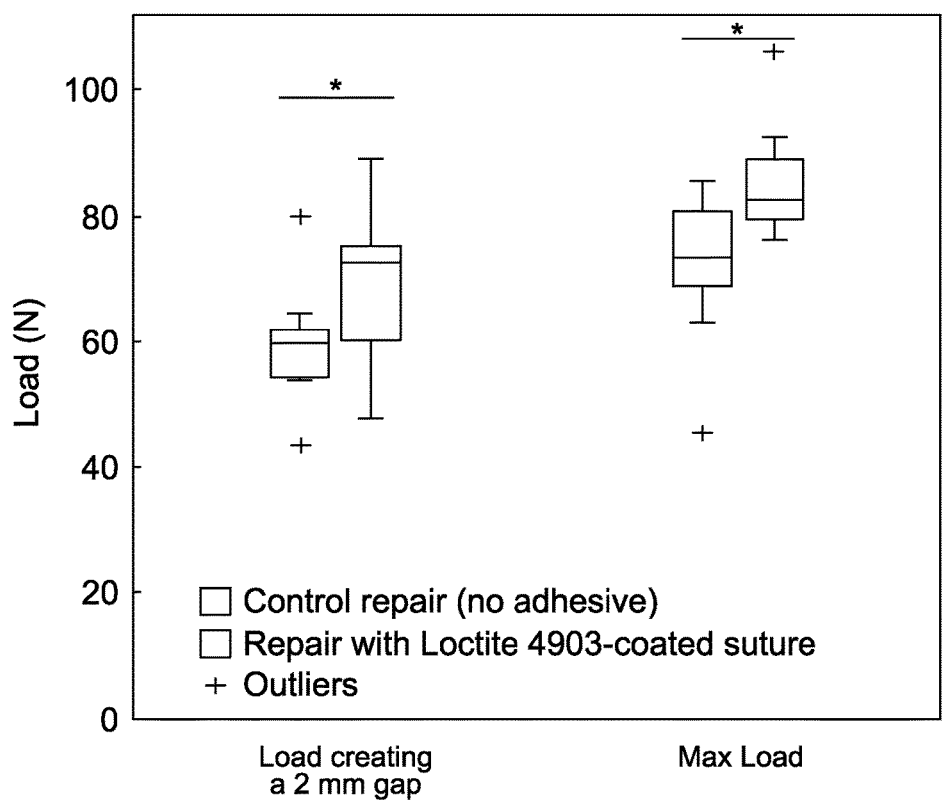
FIG. 7 is an exemplary embodiment of tendon repair load tolerance with and without adhesive in accordance with the present disclosure.

Ex vivo experiments were conducted to determine the force required to pull out example sutures including an adhesive-coated suture. FIGS. 6 and 7 illustrate the maximum load resisted by various example sutures.

FIG. 6 includes a diagram illustrating the maximum loads resisted by each suture for single suture strands coated with nothing (traditional suture), Elmer's rubber cement, 3M rubber and gasket adhesive 1300 (neoprene), Loctite Quicktite (cyanoacrylate), or Loctite 4903 (flexible cyanoacrylate).

FIG. 7 includes a diagram illustrating load creating a 2 mm gap and maximum load for a cadaveric canine flexor digitorum profundus tendon repair using standard clinical surgical technique (8 stranded repair with 4-0 Supramid suture) compared with the same repair style where suture was coated with Loctite 4903 (cyanoacrylate adhesive). The middle line within the box represents the median, the outer edges denote the 25% and 75% samples, and the whiskers extend to the extreme data points. Outliers are denoted by (+). Overbars denote statistically significant differences (p<0.05).

Referring to FIGS. 6 and 7, biomechanical tests of single strands of adhesive-coated suture within tendon tissue validated the model prediction that adhesive coatings can increase force required to pull out a suture. Loctite 4903, a "flexible" cyanoacrylate, improved the maximum load to pull out a single suture strand in tendon from about 0.076 N (±0.104 N standard deviation) without adhesive to about 3.24 N (±2.11 N standard deviation) with an adhesive-coated suture strand (shown in FIG. 6). The more compliant adhesives tested did not meaningfully increase the maximum load to pull out the suture, likely because of poor binding to suture and tissue.

In a clinically relevant 8-stranded cadaveric canine flexor tendon repair, cyanoacrylate-coated sutures increased maximum load transfer by 17.0% (Control=72.7±11.3 N; Loctite 4903=85.0±8.6 N; p=0.009) and load to create a clinically relevant 2 mm gap by 17.5% (Control=59.2±8.8 N; Loctite 4903=69.5±11.2 N; p=0.029) compared to standard 8-stranded suture repairs without adhesive coatings (shown in FIG. 7; n=11 per group). As shown in Table 1, below, resilience, stiffness, and strain at 20 N applied force did not change significantly.

Table 1 includes resilience, stiffness, and strain at 20 N applied force for a cadaveric canine flexor digitorum profundus tendon repair using standard clinical surgical technique (8 stranded repair with 4-0 Supramid suture) compared with the same repair style where suture was coated with Loctite 4903 (cyanoacrylate adhesive). The modified resilience shown in Table 1 is calculated from a force-strain curve.

TABLE 1

|  | Resilience | Stiffness | Strain at 20 N |
|---|---|---|---|
| Repair with Loctite 4903-coated suture | 9.12 ± 2.46 N | 27.2 ± 4.4 N/mm | 8.00 ± 1.36% |
| Control repair (no adhesive) | 7.39 ± 2.22 N | 24.0 ± 7.0 N/mm | 8.81 ± 2.91% |
| p-value | 0.108 | 0.251 | 0.438 |

Adhesives have been used for decades in surgical repairs to replace or augment suture for closing the skin and other tissues, including tendon. Cyanoacrylates are particularly prevalent medical adhesives, but many other adhesive types have also been used throughout the body. However, in all but one case, the adhesives have only been applied directly at or around the interface between adjoined tissues. The present disclosure is directed to load distribution improvement using an adhesive-coating along a suture's length, leading to improved load tolerance of repaired tissues. It has been demonstrated that adhesive-soaked sutures have the potential to improve load tolerance of meniscal repairs by almost 30% compared to either suture only or adhesive at the interface, only. The present disclosure is directed to a shear lag model to predict the ability of adhesive-coated sutures to improve load transfer and to identify desirable adhesive mechanical properties.

Modeling and ex vivo experimental results demonstrated that adhesive-coated sutures have the potential to improve the strength of tissue repairs, especially after development of adhesives with optimal mechanical properties. Much of the domain of adhesive physical properties evaluated (shown in FIG. 4B) is unrealistic for current biomaterials, since shear modulus and failure shear stress are related properties. When considering an Ashby plot of relevant materials, the contour map highlights potential candidate materials. While most engineering materials do not have appropriate mechanical (or biological) properties for use as an adhesive coating sutures, several elastomers such as polychloroprene, polyurethane rubber, and natural rubber do have appropriate shear moduli and shear strength to be used as base materials for adhesive development. Some biological materials, e.g., those based on elastin, could also be valuable for creating bio-adhesives. Note that the shear strength used in this model may be limited by either bulk failure within the "adhesive" material or interfacial failure between the adhesive and adherends (i.e., suture and tendon). Therefore, both the bulk adhesive mechanical properties and the strength of adhesion are crucial factors for a successful adhesive.

This shear lag model describes the importance of adhesive mechanical properties for creating a successful adhesive-coated suture; however, most currently used adhesives are not designed for this purpose. Specifically engineering an adhesive material to tightly bind suture and surrounding tissue while maintaining compliance to shear stress could lead to substantially improved adhesive-coated sutures. In addition to having appropriate mechanical properties once in place in the body, in some embodiments an adhesive-coated suture is inert for storage and surgical handling before it is placed into the body. Several potential approaches to generate adhesive coatings may be used that only activate when in place within tissue.

As discussed above, adhesives that are compliant in shear facilitate greater load transfer across the adhesive-coated suture repair before rupture by lowering stress concentrations. This is directly analogous to biomimetic mechanisms of stress transfer at the enthesis using a compliant zone. Models that optimize the modulus of an interfacial zone between tendon and bone for reducing stress concentrations produce a dip in modulus (compliant zone) prior to stiffening between the two dissimilar materials. Regions of compliance between dissimilar materials can absorb more energy and act as a toughening mechanism for the interface. Similarly, a collagen-binding adhesive that directly attaches to the suture via a small compliant layer (i.e., linker molecule such as an elastin moiety) in between the suture and the collagen-binding domain should better distribute load to minimize stress concentrations, enabling more effective load transfer across the repair.

The experiments performed herein demonstrated substantial improvements in load transfer across single strand pullout and clinically relevant tendon repairs, even though Loctite 4903 is a stiff cyanoacrylate. The 3.24 N±2.11 N failure load found experimentally for a single strand of cyanoacrylate-coated suture within tendon tissue (shown in FIG. 6) very closely matches the predicted maximum load for cyanoacrylates from the shear lag model (shown in FIG. 7). The 17% improvement in load tolerance for a complete 8-stranded repair, amounting to improvement of 10-15 N, could substantially decrease rupture rate in flexor tendon repairs.

Models appropriate for optimization of adhesive layer mechanical properties, such as the shear lag models described herein, relied on several simplifying assumptions. In the example of a shear lag model, the simplifying assumptions are as follows. First, the system is assumed to be one dimensional; only forces and stresses along the long axis of the tendon/suture are considered. This results in shear stresses that are unbalanced. Second, the deformation of the adhesive is not considered. This assumption is reasonable for stiff adhesives, but becomes an issue for highly compliant adhesives. Third, the stress in the suture and the tissue is assumed to be independent of radial position. This may be inaccurate, as the adhesive attaches only to the outside of the suture. Nevertheless, non-absorbable sutures used in tendon repair can be assumed rigid in tension compared to the failure forces of the repair. Therefore, the uniform stress distribution within the tendon is acceptable for this application. Although this will leads to errors in calculating forces through the tendon, it provides a reasonable approximation of total force transferred. Despite limitations listed above, this simplified model of suture-tendon interaction allows for determination of the design space for an adhesive-coated suture for tissue repair. When used in combination with an Ashby plot showing real material properties, this model can identify promising base materials for adhesive-coated suture development.

Improved mechanical repair techniques could improve patient outcomes not only by strengthening repairs but also by enabling more aggressive rehabilitation protocols. By holding the tissues together for longer time intervals, mechanical solutions that prevent gap formation could provide more time for the biological healing response to generate a strong, organized tissue instead of disorganized scar. In some embodiments, Loctite 4903 shows promising results that would be valuable clinically. The present disclosure is directed to adhesives with optimized mechanical and chemical properties that further increase load transfer and improve clinical repairs for tendon, ligament, and other tissue injuries.

Silk-HRP-MeOH Gels

To improve the bulk mechanical properties of the Silk-HRP hydrogels, the gels were exposed to varying concentrations of methanol. Silk-HRP hydrogels were created in accordance with the present disclosure. These Silk-HRP hydrogels were placed into methanol (MeOH) at concentrations of 10%, 50%, 70%, and 100% for 90 minutes to increase crystallinity in the silk. The gels were then placed into phosphate buffered saline overnight to rehydrate. Methanol-treated Silk-HRP gels represent one possible adhesive with attractiveness in use with sutures in tendon repair due to their biocompatibility, biodegradability, and tunable mechanical properties which allow one to obtain material properties that place the adhesive in the critical zone we have identified.

Lap Shear Test

The lap shear test is a commonly used method for testing material properties of adhesives. For testing the bulk material properties of the Silk-HRP gels and the Silk-HRP-MeOH gels, a double lap shear test was used. In this test, a single, movable PVC platen is sandwiched between two fixed platens. A slab of sample material with thickness (t) is glued with cyanoacrylate to both a fixed platen and the movable platen such that both sides of the movable platen are glued to a slab of a sample of the material being tested. In this way, two samples of material are tested simultaneously. To perform the test, the movable platen is pulled between and parallel to the fixed platens at a constant rate of 0.1 mm/sec, and the force (F) required to maintain this pulling rate is recorded. This force can be converted to a nominal shear stress ($\tau$) by dividing by the contact area between the material and the movable platen. The nominal shear strain ($\gamma$) is calculated by dividing the displacement of the movable platen (u) by the average change in the thickness (t) between the two material samples. The adhesive shear modulus $G_a$ is the nominal shear stress divided by the nominal shear strain. The adhesive failure shear stress $\tau_{fail}$ is the maximum shear stress achieved in the double lap shear test experiments.

Results

The Silk-HRP gels showed bulk mechanical properties that were sub-optimal such that they would fail as adhesives at shear stresses that were in the 1-10 kPa range, which is well below the ideal for optimal repair strength increase.

To increase the adhesive failure shear stress, Silk-HRP gels were treated with various concentrations of methanol (10%, 50%, 70%, and 100%) for 90 minutes to increase crystallinity in the silk. Results from experiments performed on Silk-HRP gels treated with MeOH (10%, 50% and 100%, respectively) are shown in FIGS. 8A (10%), 8B (50%) and 8C (100%).

There were three modes of failure during these tests: Bulk Failure, Mixed mode Failure, and Interfacial Failure. Bulk Failure indicates that the adhesive failure was due to material compromise of the bulk adhesive (the methanol treated Silk HRP gels). Interfacial Failure indicates that there was adhesive failure due to the cyanoacrylate glue at the interface of the methanol treated Silk HRP gels and the PVC platens. Mixed mode Failure means that failure occurred through a combination of Bulk Failure and Interfacial Failure. The experiments in which the samples experienced Bulk Failure are the only valid experiments for extracting the adhesive failure shear stress.

Figure 8A:
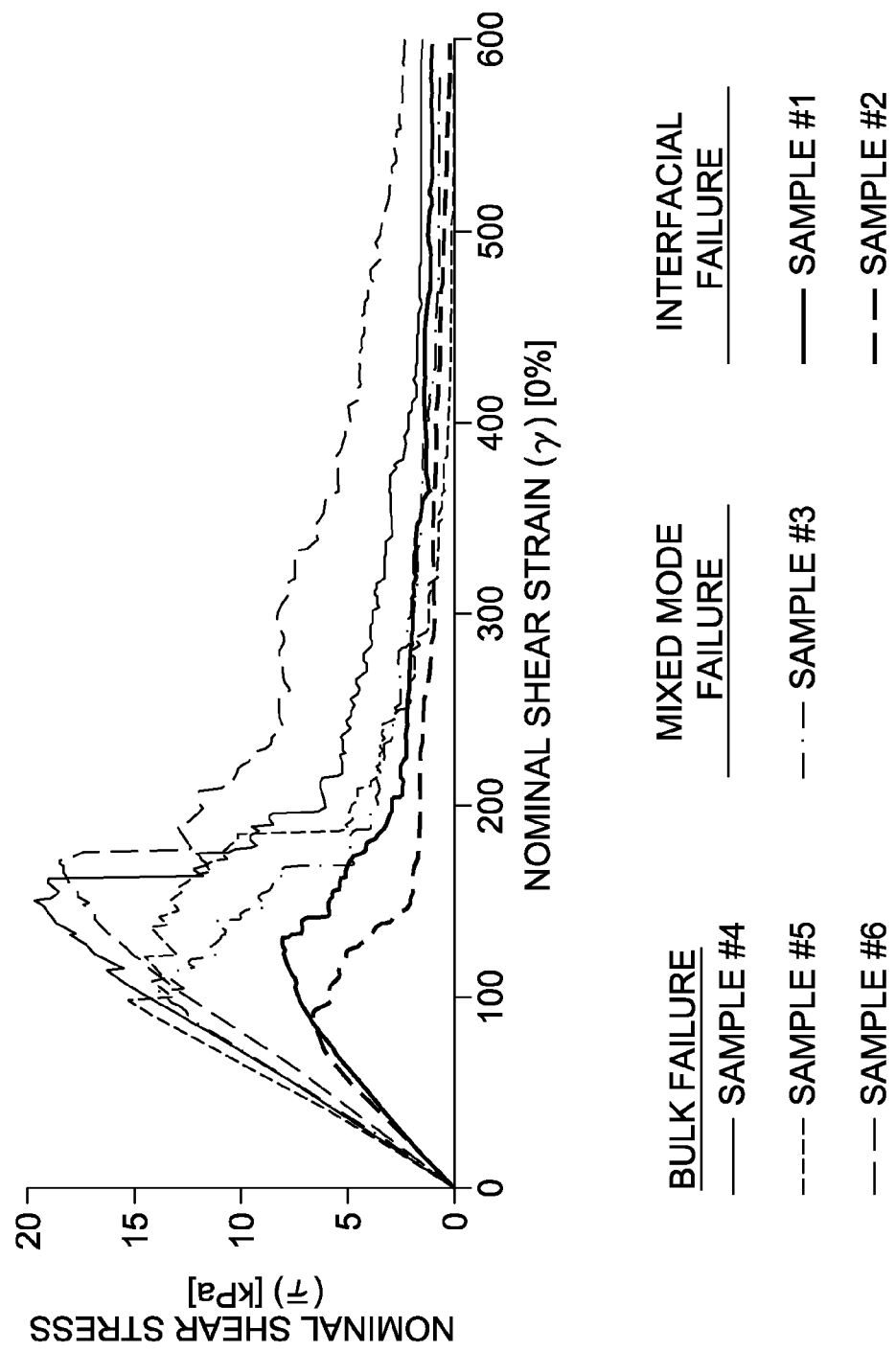
FIGS. 8A-8C are exemplary embodiments of graphical depictions of nominal shear stress vs. nominal shear strain of adhesive-coated sutures in accordance with the present disclosure.

One can see in FIG. 8A that the Silk-HRP gels treated with 10% MeOH, exhibited adhesive failure at shear stresses of approximately 15-20 kPa. This is too low to be useful for use with sutures in tendon repair.

Figure 8B:
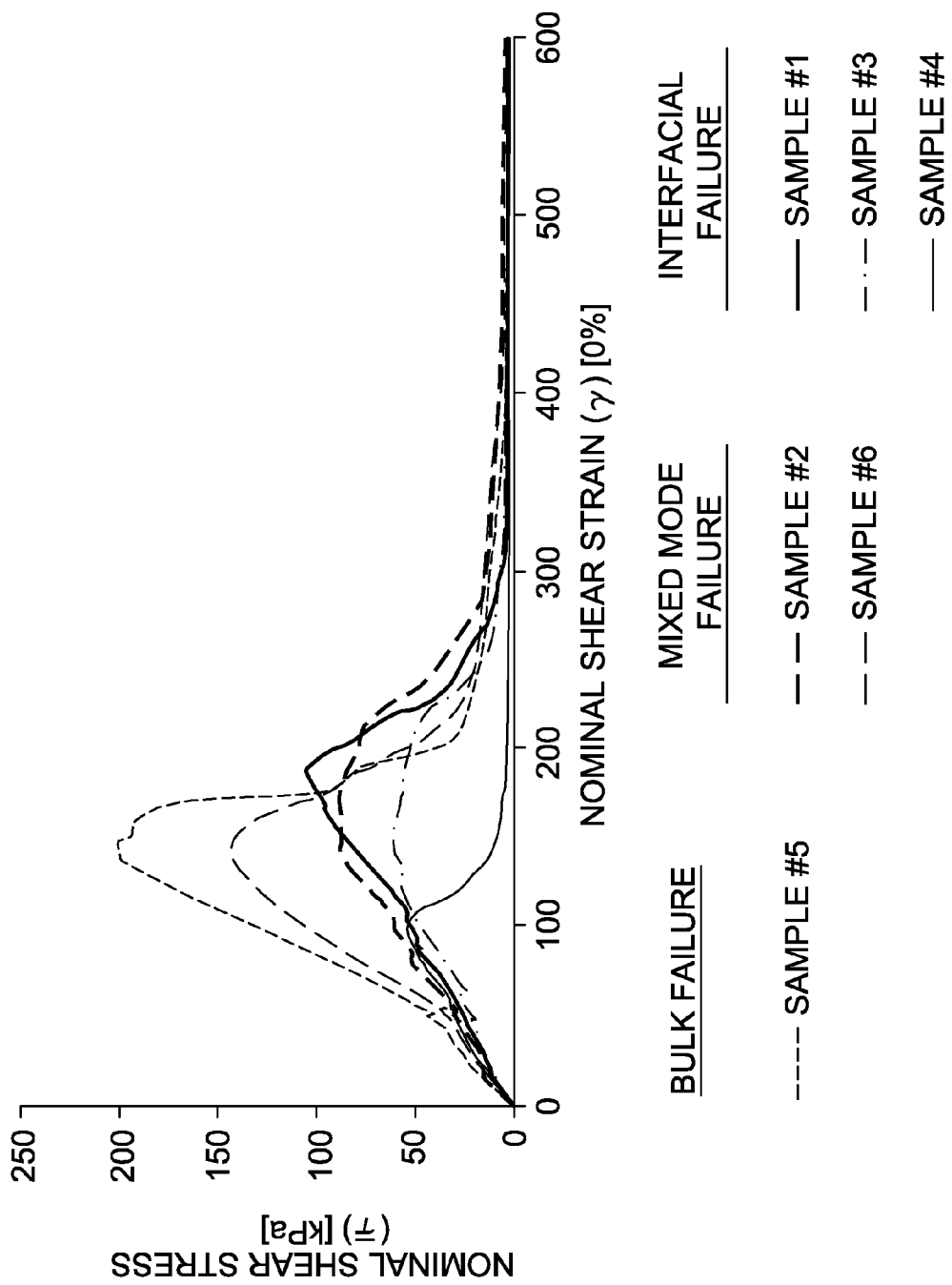
Figure 8C:
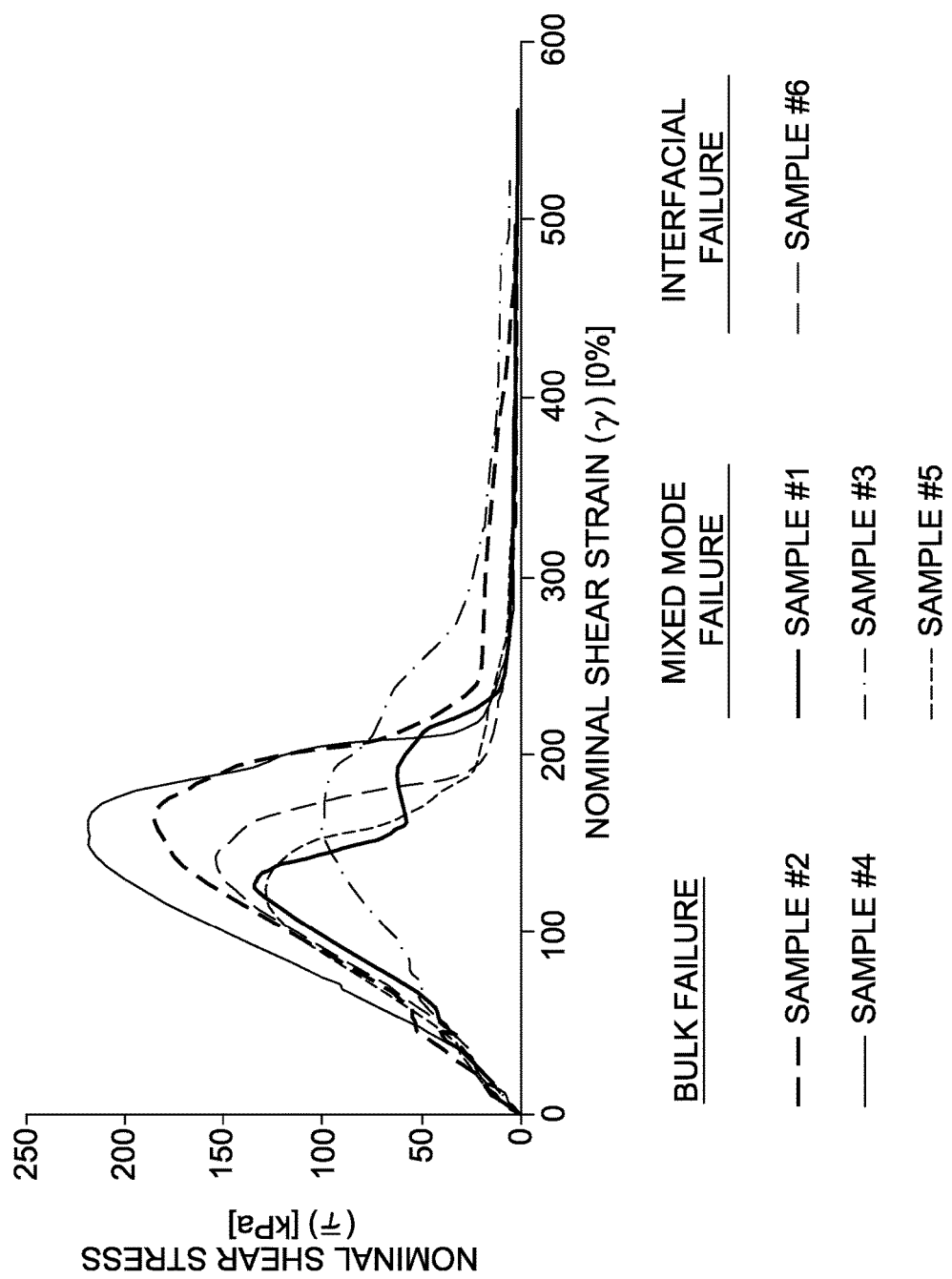

Silk HRP gels treated with 50-100% MeOH, however, exhibited adhesive failures at shear stresses of approximately 150-250 kPa as shown in FIGS. 8B and 8C. This is approaching the regime where we predict the material properties of such an adhesive would lead to repair strength increases when combined with suture.

It is important to note that the shear stress measured in these tests is actually an underestimate of the peak shear stress because the values determine in the double lap shear test represent an average over the entire material. It is likely that peak shear stresses, which are expected to occur at the edges of the material, may be an order of magnitude higher. This would place the methanol-treated Silk-HRP gels within the critical zone where we would expect sutures coated with Silk-HRP gels to enhance the repair strength in tendon.

This written description uses examples to describe the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A suture coated with an adhesive, the adhesive comprising a suture-binding domain, a compliant domain, and a tissue-binding domain linked in series, wherein the compliant domain comprises an elastin moiety linker molecule, wherein the tissue-binding domain comprises a collagen-binding domain, and wherein the collagen-binding domain comprises integrin.

2. The suture according to claim 1, wherein the adhesive is a protein-based bioadhesive.

3. The suture according to claim 1, wherein the adhesive is biodegradable.

4. The suture according to claim 1, wherein the suture-binding domain comprises a silk-binding domain.

5. The suture according to claim 1, wherein the compliant domain further comprises a protein sequence.

6. A method of surgical repair, the method comprising:
coating a suture with an adhesive, the coating comprising a suture-binding domain, a compliant domain, and a tissue-binding domain linked in series, wherein the compliant domain comprises an elastin moiety linker molecule, wherein the tissue-binding domain comprises a collagen-binding domain, and wherein the collagen-binding domain comprises integrin, and wherein the coating further comprises a protective layer,
applying the suture to a part of a body, activating the adhesive layer by applying an activating stimulus to the part of the body, and binding the suture to the part of the body.

7. The method of surgical repair according to claim 6, further comprising treating the coated suture with methanol prior to applying the suture to the part of the body.

8. The method of surgical repair according to claim 6, wherein activating the adhesive by applying an activating stimulus comprises applying heat to the part of the body.

9. The method of surgical repair according to claim 6, wherein activating the adhesive by applying an activating stimulus comprises applying near infrared radiation to the part of the body.

10. The method of surgical repair according to claim 6, wherein coating the suture with the adhesive comprises coating the suture with a protein-based bioadhesive.

11. The method of surgical repair according to claim 6, wherein coating the suture with the adhesive comprises coating the suture with a biodegradable adhesive.

12. An adhesive-coated suture, wherein the adhesive comprises a suture-binding domain, a compliant domain, and a tissue-binding domain linked in series, wherein the compliant domain comprises an elastin moiety linker molecule, wherein the tissue-binding domain comprises a collagen-binding domain, and wherein the collagen-binding domain comprises integrin, and wherein the adhesive is configured to reduce a shear stress concentration at one more or more anchor points of the suture.

13. The adhesive-coated suture according to claim 12, wherein the adhesive is a protein-based bioadhesive.

14. The adhesive-coated suture according to claim 12, wherein the adhesive is biodegradable.

15. The adhesive-coated suture according to claim 12, further comprising a protective layer.

16. The adhesive-coated suture according to claim 12, wherein the adhesive is activated by applying heat.

17. The adhesive-coated suture according to claim 12, wherein the adhesive is activated by applying near infrared radiation.

18. An adhesive-coated suture, comprising a suture-binding domain, a compliant domain, and a tissue-binding domain linked in series, wherein the compliant domain comprises an elastin moiety linker molecule, wherein the tissue-binding domain comprises a collagen-binding domain, and wherein the collagen-binding domain comprises integrin, and wherein a failure shear stress of the adhesive is greater than 106 Pa.

* * * * *

UNITED STATES PATENT AND TRADEMARK OFFICE
CERTIFICATE OF CORRECTION

PATENT NO. : 10,314,574 B2
APPLICATION NO. : 14/940541
DATED : June 11, 2019
INVENTOR(S) : Stephen W. Linderman et al.

It is certified that error appears in the above-identified patent and that said Letters Patent is hereby corrected as shown below:

In the Specification

Government Support Paragraph at Column 1, Lines 13-18 should read:
This invention was made with government support under AR060719, GM007200, and AR062947 awarded by the National Institutes of Health. The government has certain rights in the invention.

Signed and Sealed this
Sixteenth Day of July, 2019

Andrei Iancu
*Director of the United States Patent and Trademark Office*